(12) United States Patent
Bailey et al.

(10) Patent No.: US 8,680,334 B2
(45) Date of Patent: Mar. 25, 2014

(54) PROCESS FOR THE PREPARATION OF IOSIMENOL

(71) Applicant: Mallinckrodt LLC, Hazelwood, MO (US)

(72) Inventors: Allan R. Bailey, Ballwin, MO (US); Michelle M. Jones, Ofallon, MO (US); Mills T. Kneller, University City, MO (US); Alexander N. Petrov, St. Peters, MO (US); David H. White, Ballwin, MO (US); Oliver Egan, Meath (IE); Fiona Rooney, Monaghan (IE)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 13/772,572

(22) Filed: Feb. 21, 2013

(65) Prior Publication Data

US 2013/0261338 A1    Oct. 3, 2013

Related U.S. Application Data

(62) Division of application No. 12/811,833, filed as application No. PCT/US2009/030885 on Jan. 14, 2009, now Pat. No. 8,445,725.

(60) Provisional application No. 61/020,826, filed on Jan. 14, 2008.

(51) Int. Cl.
*C07C 233/05* (2006.01)
*C07C 233/65* (2006.01)

(52) U.S. Cl.
USPC ........................... 564/153; 424/9.452

(58) Field of Classification Search
USPC ........................... 564/153; 424/9.452
See application file for complete search history.

(56) References Cited

U.S. PATENT DOCUMENTS

| | | |
|---|---|---|
| 4,584,401 A | 4/1986 | Sovak et al. |
| 4,954,348 A | 9/1990 | Sovak et al. |
| 5,013,865 A | 5/1991 | Cross et al. |
| 5,075,502 A | 12/1991 | Kneller et al. |
| 5,356,613 A | 10/1994 | Lin et al. |
| 5,616,795 A | 4/1997 | Mauro et al. |
| 5,698,739 A | 12/1997 | Sovak |
| 5,763,650 A | 6/1998 | Mauro et al. |
| 5,840,967 A | 11/1998 | Gulbrandsen et al. |
| 5,958,375 A | 9/1999 | Rydeck et al. |
| 6,072,069 A | 6/2000 | Sovak et al. |
| 6,137,006 A | 10/2000 | Thieking et al. |
| 6,153,796 A | 11/2000 | Malthe-Sorensen et al. |
| 6,448,442 B1 | 9/2002 | Almen et al. |
| 6,803,485 B2 | 10/2004 | Lorenzini et al. |
| 7,250,153 B2 | 7/2007 | Sovak et al. |

FOREIGN PATENT DOCUMENTS

| | | | |
|---|---|---|---|
| CA | 2020489 | | 1/2005 |
| EP | 0406992 | | 1/1991 |
| EP | 0 406 992 | * | 3/1995 |
| EP | 0673922 | | 9/1995 |
| EP | 1186305 | | 3/2002 |

OTHER PUBLICATIONS

Gijsen et al.; "Optimisation of the Preparation and Isolation of 5-amino-2,4,6 . . . ", Organic Process Research & Development, 1999, 3 pp. 38-43.

* cited by examiner

*Primary Examiner* — Shailendra Kumar (57) ABSTRACT

A process for the preparation of iosimenol comprising reacting 5,5'-[(1,3-dioxo-1,3-propanediyl)diimino]bis[N-(2,3-dihydroxypropyl)-2,4,6-triiodo-1,3-benzenedicarboxamide] (C-VI) with a 3-halo-1,2-propanediol in an aqueous solvent. A process for the preparation of C-VI comprising reacting 3,3'-[(1,3-dioxo-1,3-propanediyl)diimino]bis[5-(aminocarbonyl)-2,4,6-triiodobenzoyl chloride] (C-V) with 3-amino-1,2-propanediol in the presence of an inorganic base and a suitable non-aqueous polar solvent. A process for the preparation of C-V comprising reacting 3-amino-5-(aminocarbonyl)-2,4,6-triiodobenzoyl chloride (C-IV) with malonyl dichloride in a solvent comprising a suitable ester solvent, a suitable nitrile solvent or mixtures thereof.

16 Claims, 5 Drawing Sheets

PROCESS FOR THE PREPARATION OF IOSIMENOL

CROSS REFERENCE TO RELATED APPLICATIONS

This application is a divisional of U.S. patent application Ser. No. 12/811,833 filed Jul. 7, 2010, now U.S. Pat. No. 8,445,725, which claims the benefit of PCT/US2009/030885, filed Jan. 14, 2009, which claims the benefit of U.S. Provisional Application No. 61/020,826 filed Jan. 14, 2008, all of which are incorporated by reference herein.

FIELD OF THE INVENTION

The present invention relates to the preparation of iosimenol, a relatively low viscosity nonionic agent for use as a contrast media in radiological procedures. The present invention also relates to the preparation of intermediates for use in the preparation of iosimenol.

BACKGROUND OF THE INVENTION

Iosimenol (5,5'-[(1,3-dioxo-1,3-propanediyl)bis[(2,3-dihydroxypropyl)imino]]bis[N-(2,3-dihydroxypropyl)-2,4,6-triiodo-1,3-benzenedicarboxamide]) has been proposed as a useful nonionic x-ray contrast agent. See, for example, U.S. Pat. No. 5,698,739 and U.S. Patent publication no. 20050025711. Processes proposed to date, however, leave room for improvement if iosimenol is to be produced in commercial quantities.

SUMMARY OF THE INVENTION

Among the various aspects of the present invention, therefore, is the provision of a process for the preparation of iosimenol in commercial quantities, the provision of a process which provides relatively high yields, and the provision of such a process which enables the use of aqueous solvents, a base and a salt to improve alkylation of the malonyl amide with 3-halo-1,2-propanediol or other appropriate alkylating agents.

Briefly, therefore, one aspect of the present invention is the preparation of iosimenol. The process comprises reacting 5,5'-[(1,3-dioxo-1,3-propanediyl)diimino]bis[N-(2,3-dihydroxypropyl)-2,4,6-triiodo-1,3-benzenedicarboxamide], Compound VI or C-VI, with a 3-halo-1,2-propanediol in an aqueous solvent, in the presence of a suitable base and a suitable additive, wherein C-VI has the formula:

The present invention is further directed to a process for the preparation of 5,5'-[(1,3-dioxo-1,3-propanediyl)diimino]bis[N-(2,3-dihydroxypropyl)-2,4,6-triiodo-1,3-benzenedicarboxamide], (C-VI). The process comprises treating 3,3'-[(1,3-dioxo-1,3-propanediyl)diimino]bis[5-(aminocarbonyl)-2,4,6-triiodobenzoyl chloride] (Compound V or C-V) with 3-amino-1,2-propanediol in the presence of a an inorganic base selected from alkali metal hydroxides, alkali metal carbonates, or combinations thereof and a suitable solvent wherein C-V has the formula:

The present invention is further directed to a process for the preparation of 3,3'-[(1,3-dioxo-1,3-propanediyl)diimino]bis[5-(aminocarbonyl)-2,4,6-triiodobenzoyl chloride] (C-V). The process comprises treating 3-amino-5-(aminocarbonyl)-2,4,6-triiodobenzoyl chloride (Compound IV or C-IV) with malonyl dichloride in a solvent system comprising a suitable ester solvent, a suitable nitrile solvent or mixtures thereof, wherein C-IV has the formula:

Other features will be in part apparent and in part pointed out hereinafter.

DETAILED DESCRIPTION OF THE INVENTION

Figure 1:
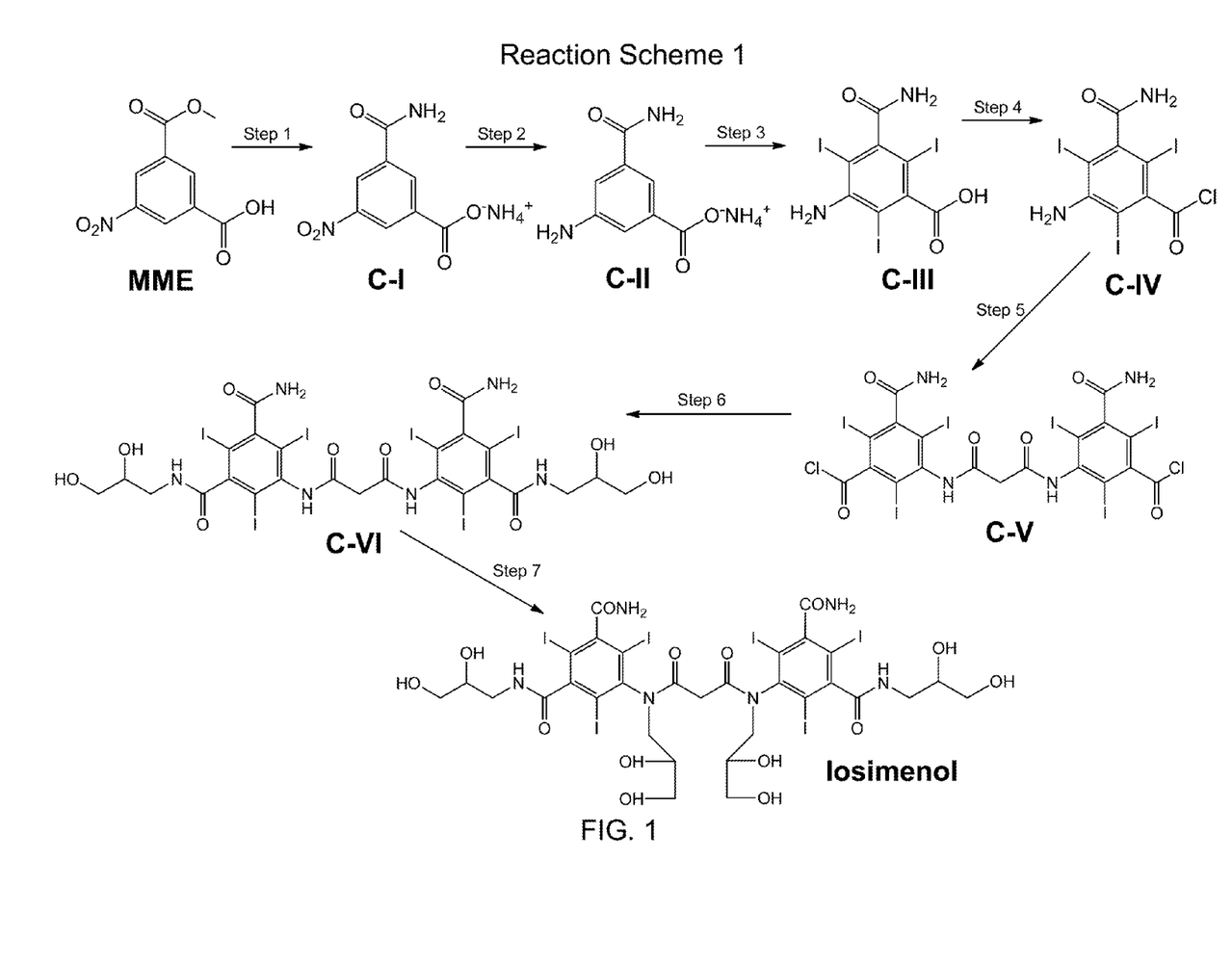
FIG. 1 is an overall reaction scheme that illustrates the preparation of iosimenol.
Figure 2:
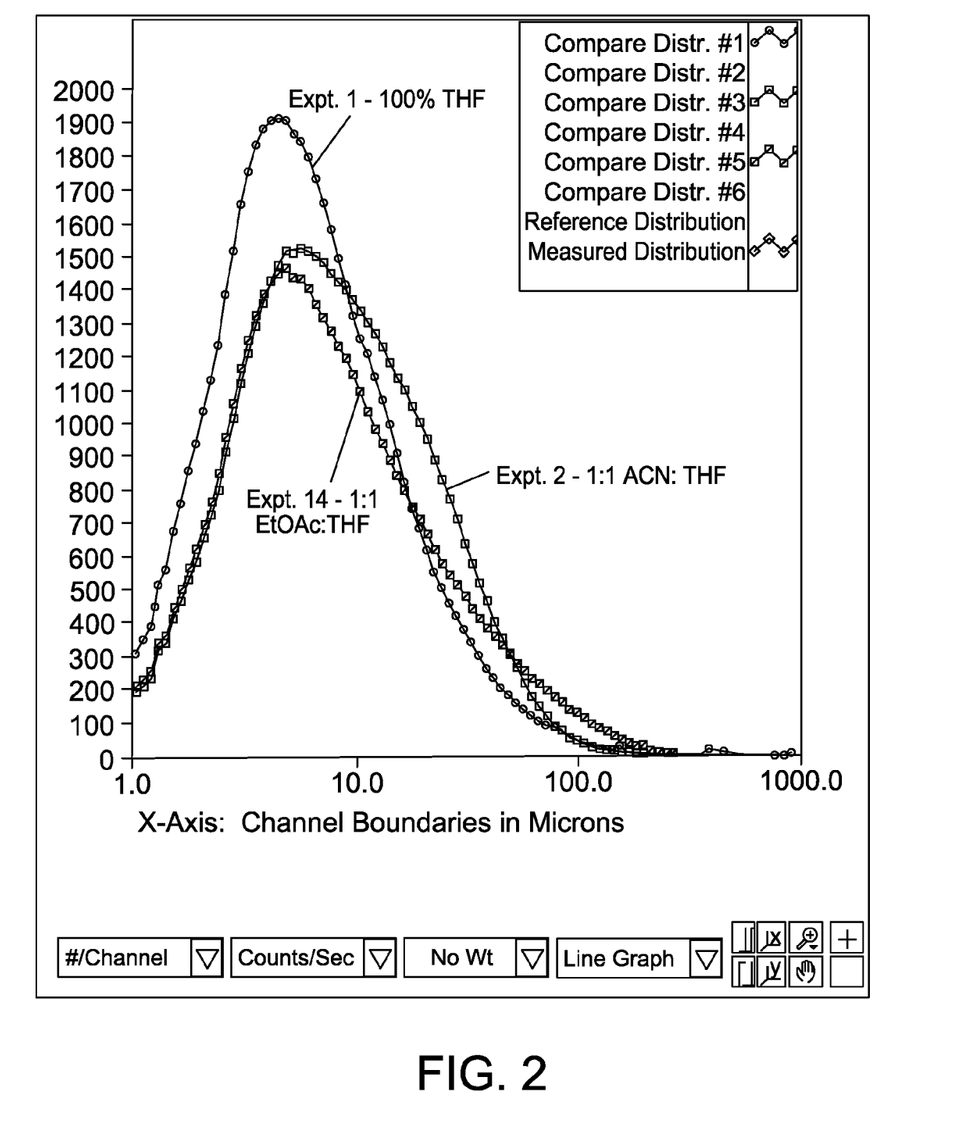
FIG. 2 is a comparison of particle size distributions from C-V reactions in Example 7 using 100% THF, 1:1 ethyl acetate: THF, and 1:1 acetonitrile: THF as solvents.
Figure 3:
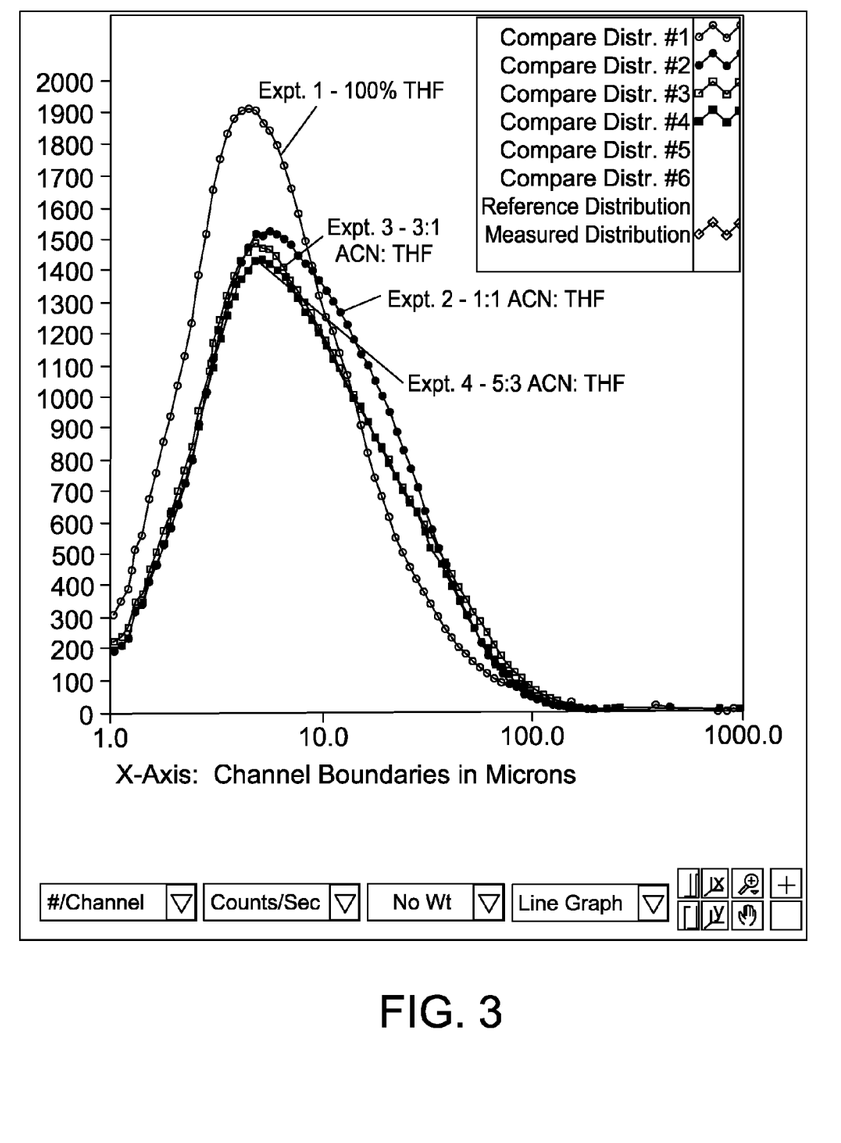
FIG. 3 is a comparison of particle size distributions from C-V reactions in Example 7 using 100% THF, 1:1 acetonitrile: THF, 3:1 acetonitrile: THF, and 5:3 acetonitrile: THF as solvents.
Figure 4:
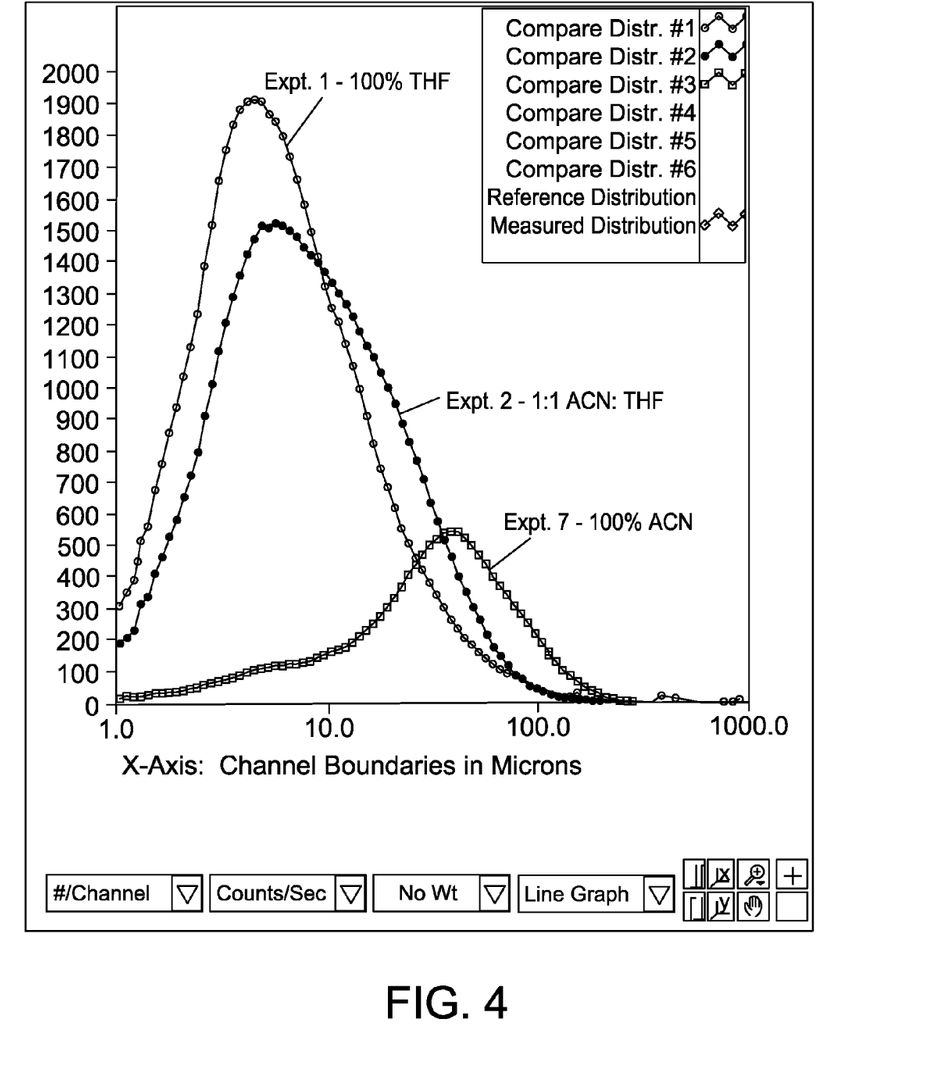
FIG. 4 is a comparison of particle size distributions from C-V reactions in Example 7 using 100% THF, 1:1 acetonitrile: THF, and 100% acetonitrile as solvents.
Figure 5:
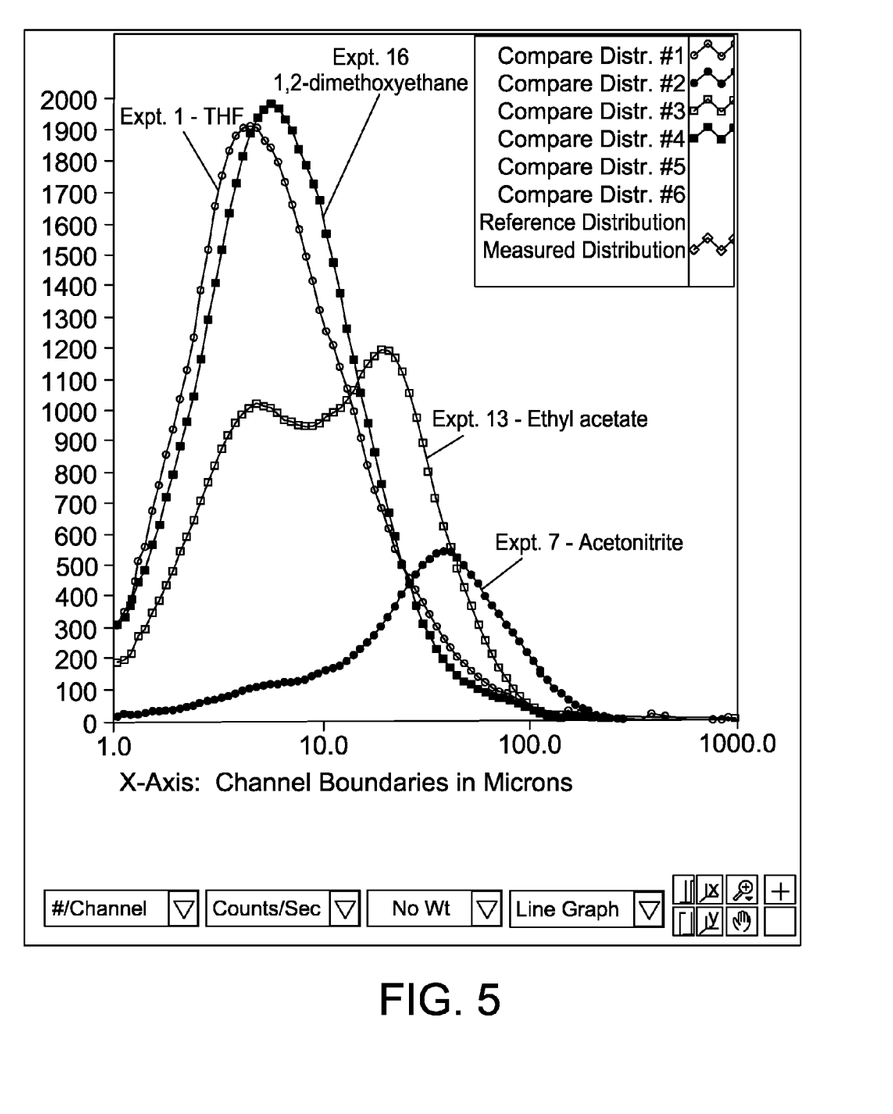
FIG. 5 is a comparison of particle size distributions for C-V reactions in Example 7 using THF, acetonitrile, ethyl acetate, and 1,2-dimethoxyethane as solvents.

Referring now to FIG. 1, Reaction Scheme 1 illustrates the preparation of iosimenol from 5-nitro-1,3-benzenedicarboxylic acid, l-methyl ester ("MME") in accordance with one aspect of the present invention. As illustrated, iosimenol is prepared in seven steps.

Step 1

The ammonium salt of 3-(aminocarbonyl)-5-nitrobenzoic acid (Compound I or C-I) is prepared from 5-nitro-1,3-benzenedicarboxylic acid, 1-methyl ester ("MME") with ammonium hydroxide. The reaction is preferably carried out in an aqueous solvent, e.g., ammonia in water, and at elevated temperatures. Preferably, the reaction mixture contains a molar excess of ammonia relative to MME. In one embodiment, the product, C-I, is obtained as a solid, centrifuged or filtered, washed with cold aqueous ammonia then by cold water and finally dried.

Step 2

3-Amino-5-(aminocarbonyl)benzoic acid (Compound II or C-II) is prepared by catalytic hydrogenation of C-I in an aqueous solvent at a temperature of 60-80° C. Preferably, the nitro group of MME is reduced with hydrogen gas in water using palladium on carbon or other suitable hydrogenation catalyst.

Step 3

3-Amino-5-(aminocarbonyl)-2,4,6-triiodobenzoic acid (Compound III or C-III) is prepared by the reaction of C-II and sodium iodine dichloride or iodine monochloride in an aqueous solvent, under acidic conditions, at a temperature of 65-85° C. The crude C-III product may be purified, for example, by reprecipitation, filtration, washing, and drying. Water can also be removed from the solid by azeotropic distillation in toluene, followed by isolation of the solid by filtration and drying.

Step 4

3-Amino-5-(aminocarbonyl)-2,4,6-triiodobenzoyl chloride (C-IV) may be prepared from the corresponding carboxylic acid, C-III, by treatment with a chlorinating reagent in the presence of a suitable solvent and a suitable catalyst. The process for the preparation of C-IV comprises treating 3-amino-5-(aminocarbonyl)-2,4,6-triiodobenzoic acid (Compound III or C-III) with a chlorinating reagent in the presence of a catalyst wherein C-III has the formula:

C-III

Exemplary chlorinating reagents include thionyl chloride, phosphorous trichloride, and phosphorous pentachloride, with thionyl chloride being currently preferred. Typically, C-III is treated with 1 to 10 molar equivalents of the chlorinating agent per equivalent of C-III, with about 1.5 to 3 equivalents being currently preferred.

The chlorination reaction may be carried out in a range of solvents. Suitable solvents include, for example, esters, chlorinated solvents, hydrocarbons, ethers, ketones and mixtures thereof. Representative esters include methyl acetate, ethyl acetate, 1-propyl acetate, 2-propyl acetate, 1-butyl acetate, 2-butyl acetate, and 2-methyl-2-propyl acetate. Representative chlorinated solvents include dichloromethane, chloroform, 1,1-dichloroethane, 1,2-dichloroethane, 1,1,1-trichloroethane, and 1,1,2-trichloroethane. Representative hydrocarbons include toluene, xylene, heptane, and cyclohexane. Representative ethers include diethyl ether, tetrahydrofuran, dioxane, dimethoxyethane, and bis-(2-methoxyethyl) ether. Representative ketones include acetone, methyl ethyl ketone, methyl isobutyl ketone, and cyclohexanone. In one embodiment, the solvent is an ester with ethyl acetate being preferred.

In general, the suitable catalyst is an amide or an amine catalyst. Exemplary catalysts include tetramethylurea, N,N-dimethylformamide, N,N-dimethylacetamide, N-methylmorpholine, N-methylpyrrolidone, 4-dimethylaminopyridine, tertiary amines, quaternary ammonium salts, and combinations thereof. In one embodiment, the catalyst is tetramethylurea.

The chlorination reaction may be carried out at a range of temperatures, typically between about 10° C. and reflux temperature (for example, >70° C. when ethyl acetate is the chlorination reaction solvent) at atmospheric pressure to a slight vacuum (e.g., 740 mm Hg). At a desired termination point, typically after 2 to 24 hours, the reaction may be quenched by introducing a quench solvent such as water, methanol, ethanol, 2-propanol, t-butanol, or other alcohol into the reaction mixture, with the amount of the quench solvent being at least about two equivalents (e.g., 2-4 equivalents) of quench solvent per molar equivalent of chlorinating agent. When ethyl acetate is used, for example, as the solvent, and thionyl chloride is used as the chlorinating agent, an intermediate, the N-sulfinyl derivative is obtained; this intermediate may then be hydrolyzed in situ, e.g., such as with water, to give the desired product. In this solvent, the reaction mixture is heterogeneous from start to finish, and C-IV may be isolated by filtration.

Step 5

3,3'-[(1,3-Dioxo-1,3-propanediyl)diimino]bis[5-(aminocarbonyl)-2,4,6-triiodobenzoyl chloride] (C-V) may be prepared by treatment of 3-amino-5-(aminocarbonyl)-2,4,6-triiodobenzoyl chloride (C-IV) with malonyl dichloride to form the dimer. Preferably, the malonyl dichloride is used in molar excess, e.g., greater than about 0.5 equivalents of malonyl dichloride for each equivalent of C-IV.

If desired, the malonyl dichloride may be prepared, in situ, by the reaction of propanedioic acid (also known as malonic acid) and phosphorous trichloride or other suitable chlorinating reagent, e.g., such as thionyl chloride or phosphorous pentachloride. In general, a slight excess of chlorinating reagent is typically used relative to the malonic acid. The molar excess of chlorinating reagent to the malonic acid is typically 0 to about 40 percent, i.e., the chlorinating reagent and malonic acid may be used at a stoichiometric level up to about a 40 percent molar excess of the chlorinating reagent. In one embodiment, the molar excess of chlorinating reagent is at least 1 percent. In another embodiment, the molar excess of chlorinating reagent is about 10 to about 30 percent, preferably about 18 to about 22 percent, and more preferably about 19 to about 21 percent.

The reaction(s) may be carried out in ethereal solvents, such as tetrahydrofuran, diethyl ether, dimethoxyethane, and methyl-t-butyl-ether, ester solvents, such as ethyl acetate, methyl acetate, n-propyl acetate, i-propyl acetate, butyl acetate and i-butyl acetate, or nitrile solvents, such as acetonitrile, propionitrile, and butyronitrile, or combinations thereof. The reaction may also be carried out in mixtures of ethereal solvents with aprotic dipolar solvents such as N,N-dimethylacetamide, N,N-dimethylformamide, N-methylpyrrolidone, and hexamethylphosphoramide. In one embodiment, the reaction is carried out in tetrahydrofuran. In another embodiment, the reaction is carried out in a solvent system comprising a suitable ester solvent, a suitable nitrile solvent or mixtures thereof. For example, the reaction is carried out in a solvent system comprising acetonitrile. Thus, for example, in this embodiment, a nitrile solvent such as acetonitrile may be used alone, or as one member of a solvent system. By way of further example, the reaction(s) may be carried out in a solvent system of acetonitrile and an ethereal solvent, e.g., tetrahydrofuran, wherein, for example, the weight ratio of acetonitrile:tetrahydrofuran is about 49:1 to about 1:9. For example, a solvent system comprising acetonitrile and tetrahydrofuran having acetonitrile:tetrahydrofuran weight ratios of about 49:1, 25:1, 9:1, 7:1, 5:1, 3:1, 2:1, 1.67:1, 1:1, 1:2, 1:3, 1:5 and 1:9 may be used. In one preferred embodiment, the weight ratio of acetonitrile:tetrahydrofuran is about 1:1 or greater, i.e., at least about 1:1. For example, a solvent system comprising acetonitrile and tetrahydrofuran having acetonitrile:tetrahydrofuran weight ratios of about 49:1, 25:1, 9:1, 7:1, 5:1, 3:1, 2:1, 1.67:1 and 1:1 may be used. In another preferred embodiment, the weight ratio of acetonitrile:tetrahydrofuran is about 3:1 to about 9:1. In yet another embodiment, for example, the reaction is carried out in a solvent system comprising an ester solvent such as ethyl acetate. Thus, for example, in this embodiment, ethyl acetate may be used alone, or as one member of a solvent system. By way of further example, the reaction(s) may be carried out in a solvent system of ethyl acetate and an ethereal solvent, e.g., tetrahydrofuran, wherein, for example, the weight ratio of ethyl acetate:tetrahydrofuran is about 49:1 to about 1:9. For example, a solvent system comprising ethyl acetate and tetrahydrofuran having ethyl acetate:tetrahydrofuran weight ratios of about 49:1, 25:1, 9:1, 7:1, 5:1, 3:1, 2:1, 1.67:1, 1:1, 1:2, 1:3, 1:5 and 1:9 may be used. In one preferred embodiment, the weight ratio of ethyl acetate:tetrahydrofuran is preferably about 1:1 or greater, i.e. at least about 1:1. For example, a solvent system comprising ethyl acetate and tetrahydrofuran having ethyl acetate:tetrahydrofuran weight ratios of about 49:1, 25:1, 9:1, 7:1, 5:1, 3:1, 2:1, 1.67:1 and 1:1 may be used. In another preferred embodiment, the weight ratio of ethyl acetate acetonitrile:tetrahydrofuran is about 3:1 to about 9:1. In yet another embodiment, the reaction(s) may be carried out in a solvent system of an ester solvent and a nitrile solvent, e.g., ethyl acetate and acetonitrile, wherein, for example, the weight ratio of ethyl acetate:acetonitrile is about 19:1 to about 1:19, preferably about 9:1 to about 1:9. For example, a solvent system comprising ethyl acetate and acetonitrile having ethyl acetate:acetonitrile weight ratios of about 19:1, 15:1, 9:1, 5:1, 3:1, 2:1, 1.67:1, 1:1, 1:2, 1:3, 1:5, 1:9, 1:15 and 1:19 may be used.

The reaction(s) may be carried out at a range of temperatures, typically between about 30 and about 80° C. for a period of about 1 to 24 hours. In one embodiment, the reaction is carried out at a temperature of about 40 to 50° C., e.g., about 45 to 50° C.

When the product, C-V, precipitates and is obtained as a solid, it may be washed with any of the suitable solvents. In one preferred embodiment, the product is washed with a non-ethereal solvent. For example, the product is washed with an ester or nitrile solvent, e.g., acetonitrile or ethyl acetate.

Step 6

5,5'-[(1,3-Dioxo-1,3-propanediyl)diimino]bis[N-(2,3-dihydroxypropyl)-2,4,6-triiodo-1,3-benzenedicarboxamide] (C-VI) may be prepared by treatment of 3,3'-[(1,3-dioxo-1,3-propanediyl)diimino]bis[5-(aminocarbonyl)-2,4,6-triiodobenzoyl chloride] (C-V) with 3-amino-1,2-propanediol in the presence of a suitable base.

A range of suitable bases may be used. In one embodiment, the base is an inorganic base selected from alkali metal hydroxides or alkali metal carbonates. Examples of suitable alkali metal hydroxides are lithium hydroxide, sodium hydroxide, or potassium hydroxide. Examples of suitable alkali metal carbonates are sodium carbonate, potassium carbonate, or lithium carbonate. In another embodiment, the base is an amine base such as triethylamine, diisopropylethylamine, tetramethylammonium hydroxide, or tetraethylammonium hydroxide. A single base may be used or alternatively, a combination of bases may be used. In one preferred embodiment, an alkali metal hydroxide is used as the suitable base.

The reaction is preferably carried out in a solvent comprising a non-aqueous polar solvent. Exemplary non-aqueous polar solvents include dimethylsulfoxide and amide solvents (e.g., N,N-dimethylformamide, N,N-dimethylacetamide, or N-methylpyrrolidone). In one embodiment, for example, the reaction is carried out in a solvent system comprising N,N-dimethylacetamide. Thus, for example, in this embodiment, N,N-dimethylacetamide may be used alone, or as one member of a solvent system. By way of further example, the reaction may be carried out in a solvent system comprising a mixture of N,N-dimethylacetamide and an ether, such as tetrahydrofuran, diethyl ether, dimethoxyethane, and methyl t-butyl ether, an ester, such as ethyl acetate, or a nitrile, such as acetonitrile.

It is generally preferred that an excess of 3-amino-1,2-propanediol be used relative to C-V. For example, approximately 2 to 3 molar equivalents of 3-amino-1,2-propanediol per equivalent of C-V will be used; with about 2.4 to about 2.6 molar equivalents of 3-amino-1,2-propanediol per equivalent of C-V being currently preferred. The reaction will typically be carried out at a temperature in the range of about 0° C. to 60° C., preferably about 10° C. to about 30° C.

In one preferred embodiment, 3,3'-[(1,3-dioxo-1,3-propanediyl)diimino]bis[5-(aminocarbonyl)-2,4,6-triiodobenzoyl chloride] (C-V) is dissolved in the solvent and 3-amino-1,2-propanediol is then introduced to form the corresponding amide. Base, preferably aqueous sodium hydroxide, is added to neutralize the byproduct, hydrogen chloride, after C-V and 3-amino-1,2-propanediol are allowed to react for a period, typically on the order of 10 to 120 minutes, preferably about 60 to 90 minutes. In general, about 1 to about 3 molar equivalents of base per mole of C-V are added; preferably, 1.8 to 2.1 molar equivalents of base per mole of C-V are added and the mixture is allowed to react for an additional period of about 1 to about 18 hours. Excess base is thereafter preferably neutralized with an acid, preferably hydrochloric acid or acetic acid. In one embodiment, the reaction mixture is thereafter concentrated, e.g., by vacuum distillation, to remove a portion of the solvent, i.e., approximately 20-60%, and typically about 50% of the solvent. The product may then be precipitated, for example, by adding a non-solubilizing solvent selected from water, preferably deionized water, 10% to 15% NaCl solution, acetone, alcohols (including, but not limited to, methanol, ethanol, 2-propanol, and t-butanol), or combination thereof to aid in precipitating the product from the concentrated mixture. Alternatively, the product may be isolated by adding base to dissolve most of the solids and then acidifying the mixture with an acid such as hydrochloric or acetic acid to reprecipitate the product. The resulting solid may then be isolated by filtration.

Step 7

Iosimenol may be prepared by reacting 5,5'-[(1,3-dioxo-1, 3-propanediyl)diimino]bis[N-(2,3-dihydroxypropyl)-2,4,6-triiodo-1,3-benzenedicarboxamide], C-VI, with a 3-halo-1,2-propanediol, preferably 3-chloro-1,2-propanediol, in an aqueous solvent in the presence of suitable base and a suitable additive. Typically, the 3-halo-1,2-propanediol will be used in molar excess relative to C-VI. For example, in one embodiment, approximately 2.5 to 5 molar equivalents of 3-chloro-1,2-propanediol will be used per equivalent of C-VI, preferably about 3.75 to about 4 molar equivalents of 3-chloro-1, 2-propanediol per equivalent of C-VI.

A range of suitable bases may be used. In one embodiment, the base is a strong inorganic base such as lithium hydroxide, sodium hydroxide, potassium hydroxide, cesium hydroxide, barium hydroxide, or strontium hydroxide. In another embodiment, the base is a carbonate such as sodium carbonate, potassium carbonate, lithium carbonate or cesium carbonate. In another embodiment, the base is an amine base such as triethylamine or diisopropylethylamine, tetramethylammonium hydroxide, or tetraethylammonium hydroxide. A single base may be used or alternatively, a combination of bases may be used. Typically, the base will be used in molar excess relative to C-VI. For example, in one embodiment, approximately 2.5 to 5 molar equivalents of base will be used per equivalent of C-VI, preferably about 3.75 to about 4 molar equivalents of base per equivalent of C-VI. The currently preferred base is sodium hydroxide.

In general, the suitable additive may be any alkali metal or alkaline earth metal salt of a halide or $C_1$-$C_6$ carboxylic acid, or combinations thereof. For purposes of the additive for use in the reaction to produce iosimenol, halide is selected from chloride, bromide or iodide. Examples of suitable additives include, but are not limited to, lithium chloride, sodium chloride, potassium chloride, cesium chloride, magnesium chloride, calcium chloride, strontium chloride, barium chloride, lithium acetate, sodium acetate, potassium acetate, cesium acetate, magnesium acetate, calcium acetate, strontium acetate, barium acetate, or the equivalent bromide, iodide, formate, propionate, 2-propenoate, butanoate, 2-methylpropanoate, pentanoate, 2,2-dimethylpropanoate or hexanoate, or combinations thereof. In one preferred embodiment, the additive is a divalent halide or acetate salt. Calcium chloride is currently preferred. Typically, the additive will be used in molar excess relative to C-VI. For example, in one embodiment, approximately 3 to 5 molar equivalents of additive are used per equivalent of C-VI, preferably about 4 molar equivalents of additive per equivalent of C-VI.

The reaction is carried out in aqueous solvent at a temperature of about 20° C. to about 70° C., preferably about 50° C. to about 55° C., for a period of about 4 to 24 hours, preferably about 8 to about 10 hours. As used herein, aqueous solvent means water or a substantially water-containing solvent system comprising water and at least one suitable co-solvent, such as, for example, $C_1$-$C_5$ mono- or di-alcohols, e.g., methanol, isopropanol, and propylene glycol, and polar aprotic solvents, e.g., tetrahydrofuran, dimethylsulfoxide, N,N-dimethylformamide, N,N-dimethylacetamide, and N-methylpyrrolidone. The pH of the reaction mixture will typically be about 8 to about 12, more preferably about 9 to about 11.

After the reaction has proceeded to the desired degree, the reaction may be quenched with acid to reduce the pH to about 5 or less; typically, the amount of acid will be about 1 to 2 molar equivalents, preferably about 1.1 molar equivalents of acid per molar equivalent of product. Suitable quench acids include acetic acid, formic acid, hydrochloric acid, sulfuric acid and combinations thereof.

In one embodiment, the quenched reaction mixture is then concentrated, e.g., by vacuum distillation, and cooled. The product, iosimenol, may be precipitated from the concentrated mixture by the addition of an alcohol, e.g., methanol, ethanol, 2-propanol, or t-butanol, acetone or other non-solubilizing solvent, or combinations thereof. The product may be further purified by conventional purification methods for x-ray contrast agents that are well known in the art.

The following non-limiting examples are provided to further illustrate the present invention.

Example 1

The Ammonium Salt of 3-(aminocarbonyl)-5-nitrobenzoic Acid

A 4000 L glass-lined reactor was charged with 22% ammonium hydroxide (2300 L) and 5-nitro-1,3-benzenedicarboxylic acid, 1-methyl ester (400 kg). The reaction mixture was heated to 40-45° C. with stirring for 2 hours. The reaction mixture was cooled to <10° C. The precipitated product was isolated by filtration. The solids were washed with cold 29% ammonium hydroxide (160 L) followed by cold water (106 L). The solids were dried at 55° C. This yielded 288 kg of the ammonium salt of 3-(aminocarbonyl)-5-nitrobenzoic acid with an assay of 95% w/w and chromatographic purity of 99.4 area %.

Example 2

3-Amino-5-(aminocarbonyl)benzoic Acid

A 4000 L glass-lined reactor was initially charged with water (913 L) and 50% wet (2.5 kg) 5% Pd/C catalyst. The reactor was then charged with 3-(aminocarbonyl)-5-nitrobenzoic acid (246 kg) and the vessel's walls were washed with additional water (487 L). The reaction mixture was heated to 65-70° C. The reactor was purged with $N_2$ and then with $H_2$. The $H_2$ pressure was set to 20-35 psig and the compound was reacted with ≈85 $m^3$ of $H_2$ for ≈3 hours. The reactor was then purged with $N_2$ and the reaction mixture was cooled to 40° C. The pH of the reaction mixture was adjusted to 8 with 30% NaOH. The catalyst was filtered from the reaction mixture and the catalyst was washed with water (55 L). The water wash was added back into the reactor. The resulting solution contained ≈213 kg of 3-amino-5-(aminocarbonyl)benzoic acid which had a chromatographic purity of 98.7 area %.

A $NaH_2PO_4$ buffer was prepared by charging water (200 L) and 30% NaOH (428 kg) into a separate vessel. While cooling, 85% $H_3PO_4$ (187 kg) was added at ≈40° C. The $NaH_2PO_4$ buffer was transferred into the reaction vessel containing the 3-amino-5-(aminocarbonyl)benzoic acid. The buffered solution of 3-amino-5-(aminocarbonyl)benzoic acid was then used in Example 3 without further transformations.

Example 3

Wet 3-amino-5-(aminocarbonyl)-2,4,6-triiodobenzoic Acid

A 0.4 kg/L ICl solution (1740 L) was prepared. A 4000 L glass-lined reactor was charged with water (2935 L) and the 3-amino-5-(aminocarbonyl)benzoic acid buffer solution (178 L) from Example 2. The reaction mixture was heated to 75° C. and 85% $H_3PO_4$ (193 L) was added. The ICl solution and the remaining 3-amino-5-(aminocarbonyl)benzoic acid buffer solution from Example 2 were added over 1 hour. The reaction mixture was stirred at 75° C. for ≈2 hours. The reaction mixture was then cooled to 40° C. to provide a solid product.

The solid product was washed with a 0.01% HCl solution (15600 L), then with a 0.01% HCl solution (15600 L) that contained $NaHSO_3$ (16.2 kg) and finally with another 0.01% HCl solution (15600 L). The solid product was dissolved by adding 30% NaOH solution (110 L) to bring the pH to ≈11. After the solution was warmed to 55° C., its pH was adjusted to 6 with acetic acid. The solution was decolorized with charcoal (22 kg). The charcoal was removed by filtration and absolute ethanol (600 L) was added. The product was precipitated by adding 15% HCl (238 L) to pH 1.7. Crude 3-amino-5-(aminocarbonyl)-2,4,6-triiodobenzoic acid was collected by filtration and washed with water (386 L). The crude wet product, 3-amino-5-(aminocarbonyl)-2,4,6-triiodobenzoic acid, had a chromatographic purity of 98.2 area %.

The crude wet 3-amino-5-(aminocarbonyl)-2,4,6-triiodobenzoic acid was dissolved in water (2080 L) by adding 50% NaOH (120 L) to give a pH of 11. The pH of the solution was adjusted to 6 by adding acetic acid (9 kg). The solution was decolorized with charcoal (22 kg) at 80° C. The charcoal was filtered off and the solution was cooled to 55° C. Absolute ethanol (600 L) was added and the product was precipitated by adding 15% HCl (238 L) to pH 1.7. Purified wet 3-amino-5-(aminocarbonyl)-2,4,6-triiodobenzoic acid was collected by filtration and washed with water (386 L). The product (605 kg) had a chromatographic purity of 98.8 area %.

Example 4

Dry 3-amino-5-(aminocarbonyl)-2,4,6-triiodobenzoic Acid

A 4000 L glass-lined reactor was charged with purified wet 3-amino-5-(aminocarbonyl)-2,4,6-triiodobenzoic acid (625 kg) and toluene (2700 kg). The mixture was heated to reflux and the water was removed by distillation. The mixture was then cooled to 30° C. and the toluene wet product was isolated by filtration. The toluene wet product was dried at 60° C. to give 361.4 kg of dry 3-amino-5-(aminocarbonyl)-2,4,6-triiodobenzoic acid which had a chromatographic purity of 99.0 area %.

Example 5

3-Amino-5-(aminocarbonyl)-2,4,6-triiodobenzoyl Chloride

A 4000 L glass-lined reactor was charged with ethyl acetate (2250 kg), 3-amino-5-(aminocarbonyl)-2,4,6-triiodobenzoic acid (1125 kg) and tetramethylurea (4.75 kg). The reaction mixture was stirred and heated to 74° C. Thionyl chloride (528 kg) was charged over 1 hour. The reaction mixture was maintained at 74° C. for 12 hours. While cooling to 45° C., additional ethyl acetate (180 kg) was charged. Water (73 kg) was charged over 1 hour and the reaction mixture was cooled to 28° C. After stirring for 7 hours, the solid product was isolated by filtration and the solids were washed with ethyl acetate (250 kg). After drying at 40° C. under vacuum, 927 kg of 3-amino-5-(aminocarbonyl)-2,4,6-triiodobenzoyl chloride were isolated which had a chromatographic purity of 92.4 area %.

Example 6

3,3'-[(1,3-Dioxo-1,3-propanediyl)diimino]bis[5-(aminocarbonyl)-2,4,6-triiodobenzoyl Chloride]

A 4000 L glass-lined reactor was charged with THF (2880 kg) and 3-amino-5-(aminocarbonyl)-2,4,6-triiodobenzoyl chloride (540 kg). The reaction mixture was heated to 45° C. and stirred until the solids dissolved. Malonic acid (47 kg) was then charged. In a second vessel $PCl_3$ (68 kg) was dissolved in THF (260 kg). The $PCl_3$/THF solution was charged to the reaction mixture over 3 hours and the reaction mixture was stirred at 45° C. for an additional 1 hour. The reaction mixture was then cooled to 25° C. and stirred for 2 hours. The product was collected by filtration and the solids were washed with THF (100 kg). The product was dried at 60° C. under vacuum to give 455 kg of 3,3'-[(1,3-dioxo-1,3-propanediyl)diimino]bis[5-(aminocarbonyl)-2,4,6-triiodobenzoyl chloride] which had a chromatographic purity of 92.5 area %.

Example 7

Preparation of 3,3'-[(1,3-dioxo-1,3-propanediyl)diimino]bis[5-(aminocarbonyl)-2,4,6-triiodobenzoyl Chloride (C-V) in Acetonitrile, Ethyl Acetate, 1,2-Dimethoxyethane (DME) and Tetrahydrofuran (THF) in Various Solvent Ratios General Procedure: Anhydrous acetonitrile (153 mL for standard reaction) was charged to a 250 mL round bottom flask equipped with overhead stirrer, temperature probe, addition funnel, condenser, and nitrogen blanket. 3-Amino-5-(aminocarbonyl)-2,4,6-triiodobenzoyl chloride (C-IV) (25.0 g, 43.4 mmol) and malonic acid (2.31 g, 22.2 mmol) were added with stirring. The solution was heated to 70-80° C., and a solution of $PCl_3$ (3.28 g, 23.8 mmol) in 13 mL anhydrous acetonitrile was added dropwise over 10-15 min. After completion of addition, the mixture was heated for an additional 4 h. The mixture was cooled to ambient temperature, vacuum filtered over Whatman #4 paper, washed with anhydrous acetonitrile (86 mL), and dried under vacuum at 30-40° C. The final solid was analyzed for % w/w assay by iodometric titration. Purity was determined by HPLC analysis on a Lichrosphere DIOL 100 5μ column at 265 nm using a gradient comprised of ethyl acetate, hexane, and THF.

This procedure was adjusted for using various combinations of acetonitrile, ethyl acetate, DME and THF as delineated in Table 1. All reactions performed using any combination of acetonitrile used acetonitrile as both diluent for $PCl_3$ and as wash solvent; for the ethyl acetate or ethyl acetate/THF reactions, ethyl acetate was used for diluent and wash solvent. For the 1,2-dimethoxyethane reaction, DME was used for diluent and wash solvent.

TABLE 1

Effect of C-V reaction conditions on yield and quality when using acetonitrile, ethyl acetate, or THF as solvent or co-solvent. Total solvent volume is given in mL/g C-IV. Yields are corrected for C-V assay. Component purities are given in % area and are uncorrected.

| Expt. | ACN proportion | THF proportion | Total solvent (mL/g) | Yield (corr.) | C-V | C-V Monoacid | C-IV | C-V Intermediate |
|---|---|---|---|---|---|---|---|---|
| 1 | 0 | 1 | 6 | 86.7 | 93.2 | 5.0 | nd | nd |
| 2 | 1 | 1 | 12 | 83.6 | 93.7 | 5.1 | 0.03 | 0.07 |
| 3 | 3 | 1 | 12 | 83.6 | 93.1 | 5.3 | 0.04 | 0.34 |
| 4 | 5 | 3 | 16 | 82.9 | 93.7 | 5.2 | 0.01 | 0.04 |
| 5 | 9 | 1 | 6 | 87.2 | 87.8 | 2.2 | 0.19 | 4.7 |
| 6 | 98 | 2 | 6 | 85.8 | 89.4 | 4.5 | 0.14 | 4.1 |
| 7 | 1 | 0 | 12 | 87.1 | 84.1 | 6.4 | 0.28 | 7.1 |
| 8 | 1 | 0 | 12 | 87.2 | 85.1 | 6.0 | 0.22 | 6.4 |
| 9 | 1 | 0 | 6 | 88.6 | 84.0 | 5.8 | 0.55 | 7.3 |
| 10 | 1 | 0 | 6 | 90.5 | 83.2 | 6.3 | 0.30 | 7.4 |
| 11 | 1 | 0 | 6 | 93.9 | 84.6 | 5.3 | 0.68 | 6.5 |
| 12 | 1 | 0 | 24 | 84.9 | 89.4 | 5.8 | 0.08 | 3.5 |
| 13 | 1 EtOAc | 0 | 6 | 91.8 | 86.3 | 4.2 | 1.1 | 6.1 |
| 14 | 1 EtOAc | 1 | 12 | 87.5 | 93.0 | 5.1 | 0.01 | 0.29 |
| 15 | 1 | 1 EtOAc | 12 | 96.1 | 89.0 | 3.7 | 0.38 | 5.5 |
| 16 | 1 DME | 0 | 6 | 94.2 | 96.0 | 3.2 | 0.08 | 0.52 | nd = not detected.
C-V Monoacid = 3-(aminocarbonyl)-5-[[3-[[3-(aminocarbonyl)-5-(chlorocarbonyl)-2,4,6-triiodophenyl]amino]-1,3-dioxopropyl]amino]-2,4,6-triiodobenzoic acid
C-V Intermediate = 3-carbamoyl-5-(3-chloro-3-oxopropanamido)-2,4,6-triiodobenzoyl chloride In situ particle size distribution was determined on selected experimental runs from Table 1 using a Lasentec Focused Beam Reflectance Measurement (FBRM) instrument with a probe inserted into stirred reaction samples. The results are shown in FIG. 2-5. The results demonstrated that use of ester and nitrile solvents alone or in mixtures with ethereal solvents produce product having larger particle size than product produced using ethereal solvents alone. With mixtures of nitrile solvents with ethereal solvents, the particle size generally increasing as the ratio of nitrile:ethereal solvent increases.

Qualitative observations of filtration rate demonstrated that significant improvement in filterability occurred at 9:1 and greater ratios of ACN:THF (Expt. 5). Qualitatively, only slight improvement in filterability was seen at lower ACN:THF ratios tested, but even slight improvements over product produced using pure THF may result in significant reductions in filtration cycle times.

The results in Table 1 also demonstrate that impurity profiles are better with lower ratios of ACN:THF, i.e., the impurity profile at 3:1 ACN:THF is significantly better than the impurity profile at 9:1 ACN:THF. The optimum combination of impurity profile and filterability is likely to occur somewhere between ACN:THF ratios of 3:1 and 9:1.

Example 8

5,5'-[(1,3-Dioxo-1,3-propanediyl)diimino]bis[N-(2,3-dihydroxypropyl)-2,4,6-triiodo-1,3-benzenedicarboxamide]

A 4000 L glass-lined reactor was charged with N,N-dimethylacetamide (968 kg) and 3,3'-[(1,3-dioxo-1,3-propanediyl)diimino]bis[5-(aminocarbonyl)-2,4,6-triiodobenzoyl chloride] (515 kg). In a separate vessel, 3-amino-1,2-propanediol (81 kg) was dissolved in N,N-dimethylacetamide (127 kg). The 3-amino-1,2-propanediol/N,N-dimethylacetamide solution was added to the stirred reaction mixture at 22° C. and the reaction mixture was stirred for 1 hour. 30% NaOH (123 kg) was then added to give a pH>9. 37% HCl (23 kg) was added to the reaction mixture to give a pH<7. The reaction mixture was heated by maintaining the reactor jacket at 100° C. and ≈230 kg of N,N-dimethylacetamide was distilled off under vacuum. Water (2680 kg) was added to the residue and stirred at 60° C. 30% NaOH (100 kg) was then added to dissolve the solids at pH>13. 37% HCl (105 kg) was then added to precipitate the product at pH<3.5. The solid product was isolated by filtration and washed with water (500 kg). The product was dried at 60° C. under vacuum to give 396 kg of 5,5'-[(1,3-dioxo-1,3-propanediyl)di imino]bis[N-(2,3-dihydroxypropyl)-2,4,6-triiodo-1,3-benzenedicarboxamide] which had a chromatographic purity of 86.5 area %.

Example 9

Crude 5,5'-[(1,3-dioxo-1,3-propanediyl)bis[(2,3-dihydroxypropyl)imino]]bis[N-(2,3-dihydroxypropyl)-2,4,6-triiodo-1,3-benzenedicarboxamide] (Iosimenol)

A CaCl₂ solution was prepared by dissolving CaCl$_2$.2H$_2$O (233 kg) in water (723 kg). A 3-chloro-1,2-propanediol (CPD) solution was prepared by dissolving 3-chloro-1,2-propanediol (176 kg) in water (176 kg). The 4000 L glass-lined reactor was charged with water (907 kg) and 5,5'-[(1,3-dioxo-1,3-propanediyl)diimino]bis[N-(2,3-dihydroxypropyl)-2,4,6-triiodo-1,3-benzenedicarboxamide] (563 kg). The pH of the slurry was adjusted to 5.5 to 7.0 with 37% HCl or 30% NaOH as needed. 50% NaOH solution (128 kg) was charged to the reaction mixture while maintaining its temperature to ≤30° C. The CaCl$_2$/water solution and then the CPD/water solution were each charged to the reaction mixture. The reaction mixture was then heated at 50° C. and stirred for ≈6 hours. 50% NaOH was added as needed to maintain the pH of the reaction at ≈10. When the reaction was complete, acetic acid (28 kg) was added to adjust the pH of the reaction mixture to 5. Using a jacket temperature of 75° C., water (1682 kg) was distilled off under vacuum. While cooling to 10° C., ethanol (2585 kg) was added to the residue in the reaction vessel. After stirring at 10° C. for 2 hours, the crude solid was collected by filtration. The solids were washed with ethanol (500 kg). The crude solid was dried at 55° C. under vacuum to give 783 kg of crude 5,5'-[(1,3-dioxo-1,3-propanediyl)bis[(2,3-dihydroxypropyl)imino]]bis[N-(2,3-dihydroxypropyl)-2,4,6-triiodo-1,3-benzenedicarboxamide]. The crude product contained 55% w/w 5,5'-[(1,3-dioxo-1,3-propanediyl)bis[(2,3-dihydroxypropyl)imino]]bis[N-(2,3-dihydroxypropyl)-2,4,6-triiodo-1,3-benzenedicarboxamide] which had a chromatographic purity of 77 area %.

Example 10

Purified 5,5'-[(1,3-dioxo-1,3-propanediyl)bis[(2,3-dihydroxypropyl)imino]]bis[N-(2,3-dihydroxypropyl)-2,4,6-triiodo-1,3-benzenedicarboxamide] (Iosimenol)

Crude iosimenol (329 kg) was added to water (1600 L) to give a mixture that contained ≈200 kg of iosimenol, ≈60 kg of related impurities and ≈140 kg of salts. The insoluble organic and inorganic impurities were removed by filtration yielding a solution which contained iosimenol, soluble organic impurities and inorganic impurities. Its conductivity was 64000 µS/cm. The solution was nanofiltered to concentrate the solution and to remove salts and low molecular weight organic impurities. The iosimenol did not pass through the membrane but remained in the retentate. The retentate contained ≈200 kg of iosimenol which had a chromatographic purity of 78.5 area % and a conductivity of 2400 µS/cm. The salts and low molecular weight organic impurities passed through the membrane and were in the permeate. The desalted iosimenol solution was deionized by passing it through a strong acid ion exchange resin and a strong base ion exchange resin. It was then decolorized with charcoal and concentrated to give a deionized solution which contained ≈200 kg of iosimenol which had a chromatographic purity of 85.2 area % and a conductivity of 13 µS/cm. The deionized iosimenol solution was purified by reverse phase chromatography using water or water/methanol to elute the product from the column. The purified fractions were concentrated, ultrafiltered using a membrane with a 10,000 Dalton molecular weight cutoff and spray dried to yield 160 kg of iosimenol with a chromatographic purity of 95 area %.

What is claimed is:

1. A process for the preparation of 3,3'-[(1,3-dioxo-1,3-propanediyl)diimino]bis[5-(aminocarbonyl)-2,4,6-triiodobenzoyl chloride] (C-V) comprising reacting 3-amino-5-(aminocarbonyl)-2,4,6-triiodobenzoyl chloride (C-IV) with malonyl dichloride in a solvent comprising a suitable ester solvent, a suitable nitrile solvent or mixtures thereof, wherein C-V and C-IV have the formulae:

C-IV

C-V

2. The process of claim 1 wherein the solvent further comprises a suitable ethereal solvent.

3. The process of claim 1 wherein the solvent is selected from acetonitrile, ethyl acetate, a mixture of acetonitrile and tetrahydrofuran, a mixture of ethyl acetate and tetrahydrofuran, a mixture of acetonitrile and 1,2-dimethoxyethane, a mixture of ethyl acetate and 1,2-dimethoxyethane, or a mixture of acetonitrile and ethyl acetate.

4. The process of claim 3 wherein the solvent is selected from acetonitrile, ethyl acetate, a mixture of acetonitrile and tetrahydrofuran, a mixture of ethyl acetate and tetrahydrofuran, or a mixture of acetonitrile and ethyl acetate.

5. The process of claim 4 wherein the solvent comprises acetonitrile or a mixture of acetonitrile and tetrahydrofuran.

6. The process of claim 5 wherein the solvent is a mixture of acetonitrile and tetrahydrofuran wherein the weight ratio of acetonitrile:tetrahydrofuran is about 1:9 to about 49:1.

7. The process of claim 6 wherein the weight ratio of acetonitrile:tetrahydrofuran is about 1:1 to about 49:1.

8. The process of claim 4 wherein the solvent is ethyl acetate or a mixture of ethyl acetate and tetrahydrofuran.

9. The process of claim 8 wherein the solvent is a mixture of ethyl acetate and tetrahydrofuran wherein the weight ratio of ethyl acetate:tetrahydrofuran is about 1:9 to about 49:1.

10. The process of claim 9 wherein the weight ratio of ethyl acetate:tetrahydrofuran is about 1:1 to about 49:1.

11. The process of claim 1 wherein compound C-V is formed as a particulate precipitate in the solvent system, and wherein the compound C-V particles have a particle size larger than compound C-V particles prepared in a solvent system comprising only ethereal solvents.

12. The process of claim 7 wherein the weight ratio of acetonitrile:tetrahydrofuran is about 3:1 to about 9:1.

13. The process of claim 10 wherein the weight ratio of ethyl acetate:tetrahydrofuran is about 3:1 to about 9:1.

14. The process of claim 5 further comprising isolating particles of compound C-V by filtration, wherein the rate of filtration is greater than the rate of filtration for compound C-V prepared in a solvent system comprising only ethereal solvents.

15. The process of claim 14 wherein the weight ratio of acetonitrile:tetrahydrofuran is about 9:1 or greater.

16. The process of claim 8 further comprising isolating particles of compound C-V by filtration, wherein the rate of filtration is greater than the rate of filtration for compound C-V prepared in a solvent system comprising only ethereal solvents.

* * * * *